United States Patent
Heer

(10) Patent No.: US 10,669,263 B2
(45) Date of Patent: Jun. 2, 2020

(54) SUBSTITUTED BENZIMIDAZOLE DERIVATIVE AS A MODULATOR OF TNF ACTIVITY

(71) Applicant: UCB Biopharma SRL, Brussels (BE)

(72) Inventor: Jag Paul Heer, Slough (GB)

(73) Assignee: UCB Biopharma SRL, Brussels (BE)

( * ) Notice: Subject to any disclaimer, the term of this patent is extended or adjusted under 35 U.S.C. 154(b) by 0 days.

(21) Appl. No.: 16/349,734

(22) PCT Filed: Dec. 8, 2017

(86) PCT No.: PCT/EP2017/082092
§ 371 (c)(1),
(2) Date: May 14, 2019

(87) PCT Pub. No.: WO2018/104534
PCT Pub. Date: Jun. 14, 2018

(65) Prior Publication Data
US 2019/0284170 A1    Sep. 19, 2019

(30) Foreign Application Priority Data

Dec. 9, 2016   (GB) ................................ 1620948.8

(51) Int. Cl.
| | | |
|---|---|---|
| *A61K 31/506* | (2006.01) | |
| *A61K 31/4184* | (2006.01) | |
| *C07D 403/04* | (2006.01) | |
| *A61P 37/00* | (2006.01) | |
| *A61P 25/28* | (2006.01) | |
| *A61P 3/00* | (2006.01) | |
| *A61P 9/00* | (2006.01) | |
| *A61P 37/08* | (2006.01) | |
| *A61P 29/00* | (2006.01) | |
| *A61P 35/00* | (2006.01) | |

(52) U.S. Cl.
CPC .......... *C07D 403/04* (2013.01); *A61K 31/506* (2013.01); *A61P 3/00* (2018.01); *A61P 9/00* (2018.01); *A61P 25/28* (2018.01); *A61P 29/00* (2018.01); *A61P 35/00* (2018.01); *A61P 37/00* (2018.01); *A61P 37/08* (2018.01)

(58) Field of Classification Search
CPC .............. A61K 31/506; A61K 31/4184; C07D 403/04; A61P 37/00; A61P 25/28; A61P 3/00; A61P 9/00; A61P 37/08; A61P 29/00; A61P 35/00
USPC ............................... 514/394, 256; 548/306.1
See application file for complete search history.

(56) References Cited

FOREIGN PATENT DOCUMENTS

| WO | 2013/186229 | 12/2013 | |
|---|---|---|---|
| WO | WO-2013186229 A1 * | 12/2013 | ......... A61K 31/4439 |
| WO | 2016/050975 | 4/2016 | |

OTHER PUBLICATIONS

Tansey and Szymkowski, "The TNF superfamily in 2009: new pathways, new indications, and new drugs", Drug Discovery Today, vol. 14, Nos. 23/24, Dec. 2009, pp. 1082-1088.
Carneiro et al., "Emerging Role for TNF-a in Erectile Dysfundtion", J Sex Med, 2010, 7:3823-3834.
Wu et al., "Do TNF Inhibitors Reduce the Risk of Myocardial Infarction in Psoriasis Patients?", JAMA, May 15, 2013, vol. 309, No. 19, pp. 2043-2044.
Hauwermeiren et al., "Safe TNF-based antitumor therapy following p55TNFR reduction in intestinal epithelim", The Journal of Clinical Investigation, vol. 123, No. 6, Jun. 2013, pp. 2590-2603.
International Search Report for International Application No. PCT/EP2017/082092 dated Jan. 17, 2018, 2 pages.

* cited by examiner

*Primary Examiner* — Matthew P Coughlin
*Assistant Examiner* — Sagar Patel
(74) *Attorney, Agent, or Firm* — McDonnell Boehnen Hulbert & Berghoff LLP

(57) ABSTRACT

2-(5-{1-[2-(Difluoromethoxy)-6-fluorobenzyl]-2-methyl-1H-benzimidazol-6-yl}pyrimidin-2-yl)propan-2-ol, or a pharmaceutically acceptable salt thereof, being potent modulators of human TNFα activity, are accordingly of benefit in the treatment and/or prevention of various human ailments, including autoimmune and inflammatory disorders; neurological and neurodegenerative disorders; pain and nociceptive disorders; cardiovascular disorders; metabolic disorders; ocular disorders; and oncological disorders.

5 Claims, No Drawings

SUBSTITUTED BENZIMIDAZOLE DERIVATIVE AS A MODULATOR OF TNF ACTIVITY

CROSS-REFERENCE TO RELATED APPLICATIONS

This application is the US national phase under 35 U.S.C. § 371 of International Patent Application No. PCT/EP2017/082092 filed on Dec. 8, 2017, which claims the benefit of Great Britain Application No. 1620948.8, filed Dec. 9, 2016, the entirety of each of the foregoing applications is hereby incorporated by reference into the present specification.

The present invention relates to a substituted fused imidazole derivative, and to its use in therapy. More particularly, this invention is concerned with a pharmacologically active substituted 1H-benzimidazole derivative. This compound acts as a modulator of the signalling of TNFα, and is accordingly of benefit as a pharmaceutical agent, especially in the treatment of adverse inflammatory and autoimmune disorders, neurological and neurodegenerative disorders, pain and nociceptive disorders, cardiovascular disorders, metabolic disorders, ocular disorders, and oncological disorders.

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certolizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today*, 2009, 14, 1082-1088; and F. S. Carneiro et al., *J. Sexual Medicine*, 2010, 7, 3823-3834).

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, the compounds of this invention may be useful for coupling to a fluorophore to provide fluorescent conjugates that can be utilised in assays (e.g. a fluorescence polarisation assay) for detecting pharmacologically active compounds.

WO 2013/186229 describes a class of benzimidazole derivatives which are stated to be modulators of TNFα signalling beneficial in the treatment of adverse inflammatory and autoimmune disorders, neurological and neurodegenerative disorders, pain and nociceptive disorders, cardiovascular disorders, metabolic disorders, ocular disorders, and oncological disorders.

The present invention provides 2-(5-{1-[2-(difluoromethoxy)-6-fluorobenzyl]-2-methyl-1H-benzimidazol-6-yl}pyrimidin-2-yl)propan-2-ol of formula (I):

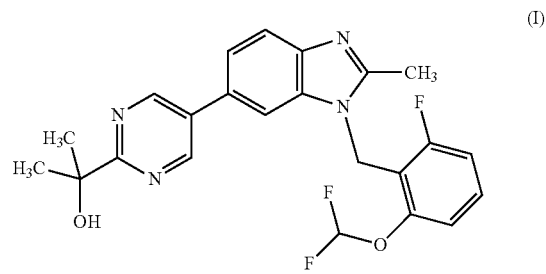 [SMILES: Cc1nc2ccc(-c3cnc(C(C)(C)O)nc3)cc2n1Cc1c(F)cccc1OC(F)F]

or a pharmaceutically acceptable salt thereof.

The compounds in accordance with the present invention are encompassed within the generic scope of WO 2013/186229. There is, however, no specific disclosure therein of the compound of formula (I) as depicted above, or a pharmaceutically acceptable salt thereof.

The present invention also provides the compound of formula (I) as depicted above, or a pharmaceutically acceptable salt thereof, for use in therapy.

The present invention also provides the compound of formula (I) as depicted above, or a pharmaceutically acceptable salt thereof, for use in the treatment and/or prevention of disorders for which the administration of a modulator of TNFα function is indicated.

In another aspect, the present invention provides the compound of formula (I) as depicted above, or a pharmaceutically acceptable salt thereof, for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides the use of the compound of formula (I) as depicted above, or a pharmaceutically acceptable salt thereof, for the manufacture of a medicament for the treatment and/or prevention of disorders for which the administration of a modulator of TNFα function is indicated.

In another aspect, the present invention provides the use of the compound of formula (I) as depicted above, or a pharmaceutically acceptable salt thereof, for the manufacture of a medicament for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of the compound of formula (I) as depicted above, or a pharmaceutically acceptable salt thereof.

In another aspect, the present invention provides a method for the treatment and/or prevention of an inflammatory or autoimmune disorder, a neurological or neuro-degenerative disorder, pain or a nociceptive disorder, a cardiovascular disorder, a metabolic disorder, an ocular disorder, or an oncological disorder, which comprises administering to a patient in need of such treatment an effective amount of the compound of formula (I) as depicted above, or a pharmaceutically acceptable salt thereof.

For use in medicine, the salts of the compound of formula (I) will be pharmaceutically acceptable salts. Other salts may, however, be useful in the preparation of the compound of formula (I) or of its pharmaceutically acceptable salts. Standard principles underlying the selection and preparation of pharmaceutically acceptable salts are described, for example, in *Handbook of Pharmaceutical Salts: Properties, Selection and Use,* ed. P. H. Stahl & C. G. Wermuth, Wiley-VCH, 2002. Suitable pharmaceutically acceptable salts of the compound of formula (I) include acid addition salts which may, for example, be formed by mixing a solution of the compound of formula (I) with a solution of a pharmaceutically acceptable acid.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, inflammatory myopathy (including polymyositis, dermatomyositis and inclusion body myositis), scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behcet's disease and Sjogren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy), organ transplant rejection (including kidney allograft rejection), scleritis (including giant cell arteritis scleritis), Takayasu arteritis, hidradenitis suppurativa, pyoderma gangrenosum, sarcoidosis, polymyalgia rheumatic and axial spondyloarthritis.

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA*, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy and retinopathy of prematurity), macular oedema (including diabetic macular oedema), age-related macular degeneration (ARMD), vascularisation (including corneal vascularisation and neovascularisation), retinal vein occlusion, and various forms of uveitis (including iritis) and keratitis.

Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.*, 2013, 123, 2590-2603).

The present invention also provides a pharmaceutical composition which comprises the compound of formula (I) as depicted above, or a pharmaceutically acceptable salt thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compound of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compound of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate.

Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule.

The compound of formula (I) above may be prepared by a process which comprises reacting a compound of formula (III) with a compound of formula (IV):

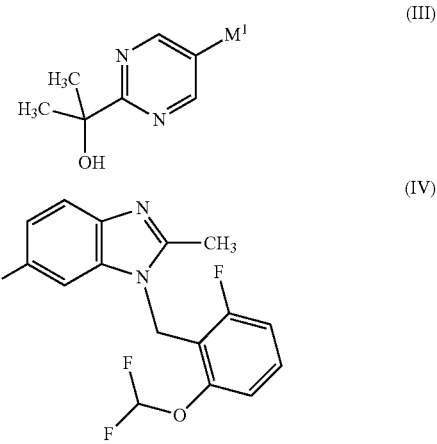

wherein L¹ represents a suitable leaving group, and M¹ represents a boronic acid moiety —B(OH)₂ or a cyclic ester thereof formed with an organic diol, e.g. pinacol, 1,3-propane-diol or neopentyl glycol; in the presence of a transition metal catalyst.

The leaving group L¹ is typically a halogen atom, e.g. bromo.

The transition metal catalyst of use in the reaction between compound (III) and (IV) is suitably [1,1'-bis(diphenylphosphino)ferrocene]dichloropalladium(II), dichloro[1,1'-bis(di-tert-butylphosphino)ferrocene]palladium(II), tetrakis(triphenyl-phosphine)palladium(0), or bis[3-(diphenylphosphanyl)cyclopenta-2,4-dien-1-yl]iron-dichloropalladium-dichloromethane complex. The reaction is suitably performed in the presence of a base, e.g. an inorganic base such as sodium carbonate or potassium carbonate, or potassium phosphate. The reaction is conveniently carried out at an elevated temperature in a suitable solvent, e.g. a cyclic ether such as 1,4-dioxane.

The intermediates of formula (IV) above may be prepared by a two-step process which comprises: (i) reducing the nitro group in a compound of formula (V):

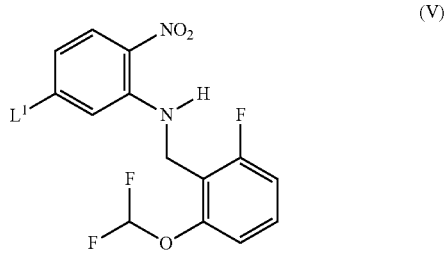

wherein L¹ is as defined above; and (ii) reacting the amine derivative thereby obtained with acetic acid.

Step (i) of the foregoing procedure can be conveniently effected by catalytic hydrogenation of compound (V), which typically comprises treating compound (V) with gaseous hydrogen in the presence of a hydrogenation catalyst such as palladium on carbon.

Alternatively, the reduction of compound (V) may be effected by treatment with elemental iron or zinc, typically at an elevated temperature in the presence of acetic acid.

Alternatively, the reduction of compound (V) may be effected by treatment with tin(II) chloride, typically at an elevated temperature in the presence of a mineral acid such as hydrochloric acid.

Step (ii) of the foregoing procedure is conveniently effected by heating the resulting amine derivative in acetic acid.

The intermediates of formula (V) above may be prepared by reacting a compound of formula (VI) with a compound of formula (VII):

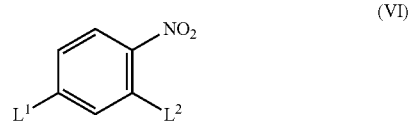

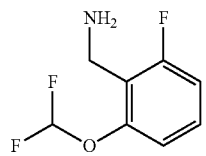

wherein L¹ is as defined above, and L² represents a displaceable group.

The displaceable group L² is typically a halogen atom, e.g. fluoro.

The reaction is suitably performed in the presence of a base, e.g. an inorganic base such as potassium carbonate. The reaction is conveniently carried out at an elevated temperature in a suitable solvent, e.g., a cyclic amine such as 1-methyl-2-pyrrolidinone.

Where they are not commercially available, the starting materials of formula (III), (VI) and (VII) may be prepared by methods analogous to those described in the accompanying Examples, or by standard methods well known from the art.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at any convenient subsequent stage utilising methods known from the art.

The compounds in accordance with the present invention potently neutralise the activity of TNFα in a commercially available HEK-293 derived reporter cell line known as HEK-Blue™ CD40L. This is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, also referred to herein as the reporter gene assay, the compounds of the present invention exhibit an $IC_{50}$ value better than 50 nM.

The compounds in accordance with the present invention potently inhibit the binding of a fluorescence conjugate to TNFα when tested in the fluorescence polarisation assay described herein. Indeed, when tested in that assay, the compounds of the present invention exhibit an $IC_{50}$ so value better than 20 nM.

Fluorescence Polarisation Assay
Preparation of Compound (A)
1-(2,5-Dimethylbenzyl)-6-[4-(piperazin-1-ylmethyl)phenyl]-2-(pyridin-4-yl-methyl)-1H-benzimidazole—hereinafter referred to as "Compound (A)"—can be prepared by the procedure described in Example 499 of WO 2013/186229; or by a procedure analogous thereto.

Preparation of Fluorescence Conjugate
Compound (A) (27.02 mg, 0.0538 mmol) was dissolved in DMSO (2 mL). 5 (−6) Carboxy-fluorescein succinimyl ester (24.16 mg, 0.0510 mmol) (Invitrogen catalogue number: C1311) was dissolved in DMSO (1 mL) to give a bright yellow solution. The two solutions were mixed at room temperature, the mixture turning red in colour. The mixture was stirred at room temperature. Shortly after mixing a 20 µL aliquot was removed and diluted in a 80:20 mixture of AcOH:H$_2$O for LC-MS analysis on the 1200RR-6140 LC-MS system. The chromatogram showed two closely eluting peaks at retention times of 1.42 and 1.50 minutes, both with mass (M+H)$^+$=860.8 amu, corresponding to the two products formed with the 5- and 6-substituted carboxyfluorescein group. A further peak at retention time 2.21 minutes had a mass of (M+H)$^+$=502.8 amu, corresponding to Compound (A). No peak was observed for unreacted 5(-6) carboxyfluorescein succinimyl ester. The peak areas were 22.0%, 39.6% and 31.4% for the three signals, indicating a 61.6% conversion to the two isomers of the desired fluorescence conjugate at that time-point. Further 20 µL aliquots were extracted after several hours and then after overnight stirring, diluted as before and subjected to LC-MS analysis. The percentage conversion was determined as 79.8% and 88.6% respectively at these time-points. The mixture was purified on a UV-directed preparative HPLC system. The pooled purified fractions were freeze-dried to remove excess solvent. After freeze-drying, an orange solid (23.3 mg) was recovered, equivalent to 0.027 mmol of fluorescence conjugate, corresponding to an overall yield of 53% for the reaction and preparative HPLC purification.

Inhibition of Binding of Fluorescence Conjugate to TNFα

Compounds were tested at 10 concentrations starting from 25 µM in a final assay concentration of 5% DMSO, by pre-incubation with TNFα for 60 minutes at ambient temperature in 20 mM Tris, 150 mM NaCl, 0.05% Tween 20, before addition of the fluorescence conjugate and a further incubation for 20 hours at ambient temperature. The final concentrations of TNFα and the fluorescence conjugate were 10 nM and 10 nM respectively in a total assay volume of 25 µL. Plates were read on a plate reader capable of detecting fluorescence polarisation (e.g. an Analyst HT plate reader; or an Envision plate reader). An IC$_{50}$ value was calculated using XLfit™ (4 parameter logistic model) in ActivityBase.

When tested in the fluorescence polarisation assay, the compound of the accompanying Example was found to exhibit an IC$_{50}$ value better than 20 nM.

Thus, when tested in the fluorescence polarisation assay, the compound of the accompanying Example was found to exhibit an IC$_{50}$ value between 0.1 nM and 20 nM.

Reporter Gene Assay
Inhibition of TNFα-induced NF-κB Activation

Stimulation of HEK-293 cells by TNFα leads to activation of the NF-κB pathway. The reporter cell line used to determine TNFα activity was purchased from InvivoGen. HEK-Blue™ CD40L is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a dose-dependent manner by TNFα, with an EC50 of 0.5 ng/mL for human TNFα. Compounds were diluted from 10 mM DMSO stocks (final assay concentration 0.3% DMSO) to generate a 10-point 3-fold serial dilution curve (e.g. 30,000 nM to 2 nM final concentration). Diluted compound was preincubated with TNFα for 60 minutes prior to addition to a 384-well microtitre plate and incubated for 18 h. The final TNFα concentration in the assay plate was 0.5 ng/mL. SEAP activity was determined in the supernatant using a colorimetric substrate, e.g. QUANTI-Blue™ or HEK-Blue™ Detection media (InvivoGen). Percentage inhibitions for compound dilutions were calculated between a DMSO control and maximum inhibition (by excess control compound) and an IC$_{50}$ value calculated using XLfit™ (4 parameter logistic model) in ActivityBase.

When tested in the reporter gene assay, the compound of the accompanying Example was found to exhibit an IC$_{50}$ value better than 50 nM.

Thus, when tested in the reporter gene assay, the compound of the accompanying Example was found to exhibit an IC$_{50}$ value between 0.5 nM and 50 nM.

The following Example illustrates the preparation of the compound according to the invention.

EXAMPLES

Abbreviations
DCM: dichloromethane EtOAc: ethyl acetate
DMSO: dimethylsulfoxide h: hour
LCMS: Liquid Chromatography Mass Spectrometry
GCMS: Gas Chromatography Mass Spectrometry
M: mass RT: retention time
Nomenclature
Compounds were named with the aid of ACD/Name Batch (Network) version 12.0, and/or Accelrys Draw 4.0.
Analytical Conditions
LCMS
Method 1
Waters Acquity-SQD, Waters Acquity UPLC BEH C18, 2.1×50 mm, 1.7 µm column
Mobile phase A: 10 mM ammonium formate+0.1% ammonia
Mobile phase B: 95% acetonitrile+5% H$_2$O+0.1% ammonia
Flow Rate: 1.0 mL/min
Column Temperature: 40° C.

| Gradient program | | |
| --- | --- | --- |
| Time | A % | B % |
| 0.00 | 95 | 5 |
| 0.50 | 95 | 5 |
| 1.75 | 5 | 95 |
| 2.00 | 5 | 95 |
| 2.25 | 95 | 5 |

LCMS SC_ACID
Column: Waters XSelect (C18, 30×2.1 mm, 3.5 µm) valve: 1
Flow Rate: 1 mL/minute
Column Temperature: 35° C.
Eluent A: 0.1% formic acid in acetonitrile
Eluent B: 0.1% formic acid in water
Lin. Gradient: t=0 min 5% A, t=1.6 min 98% A, t=3 min 98% A
Detection: DAD (220-320 nm)
Detection: MSD (ESI pos/neg) mass range: 100-800
Detection: ELSD (PL-ELS 2100): gasflow 1.2 mL/min, gas temp: 70° C., neb: 50° C.
LCMS AN_ACID
Column: Waters XSelect (C18, 50×2.1 mm, 3.5 µm) valve: 2
Flow Rate: 0.8 mL/minute
Column Temperature: 35° C.
Eluent A: 0.1% formic acid in acetonitrile
Eluent B: 0.1% formic acid in water Lin. Gradient: t=0 min 5% A, t=3.5 min 98% A, t=6 min 98% A
Detection: DAD (220-320 nm)
Detection: MSD (ESI pos/neg) mass range: 100-800
Detection: ELSD (PL-ELS 2100): gasflow 1.2 mL/min, gas temp: 70° C., neb: 50° C.
GCMS
Method S
Instrument: Agilent 6890N
Column: RXi-5MS 20 m, ID 180 μm, df 0.18 μm

| | | |
|---|---|---|
| Average velocity: 50 cm/s | Carrier gas: He | Solvent delay: 1.3 min |
| Initial temp: 60° C. | Initial time: 1.0 min | Final time: 3.5 min |
| Rate: 50° C./min | Final temp: 250° C. | Injection vol.: 1 μL |
| Split ratio: 20:1 | Injector temp: 250° C. | Mass range: 50-550 |
| Detection: MSD (EI-positive) | Detector temp.: 280° C. | |
| Detection: FID | Detector temp.: 300° C. | |

Intermediate 1

2-(Difluoromethoxy)-6-fluorobenzonitrile

To a solution of 2-fluoro-6-hydroxybenzonitrile (14.78 g, 108 mmol) in 1,4-dioxane (120 mL) was added sodium hydroxide (25.9 g, 647 mmol) in water (120 mL). The mixture was heated at 65° C. and chlorodifluoromethane (13.98 g, 162 mmol) was passed through the solution via a filter candle. The reaction mixture was allowed to cool to room temperature and the formed precipitants were filtered off. The layers of the filtrate were separated and the organic phase was combined with the organic layer from a repeat of the same experiment, starting from 2-fluoro-6-hydroxybenzonitrile (20.0 g, 146 mmol). The combined organic layer was washed with brine (2×100 mL), dried ($Na_2SO_4$), filtered and concentrated in vacuo. The resulting suspension was diluted with diethyl ether (80 mL), and washed with water (3×40 mL) and brine (2×40 mL), then dried ($Na_2SO_4$), filtered and concentrated in vacuo, to give the title compound (34.2 g, 68%) as a yellow oil, which was used without further purification. $\delta_H$(300 MHz, DMSO-$d_6$) 7.88 (td, J 8.6, 6.8 Hz, 1H), 7.50 (t, J 72.0 Hz, 1H), 7.43 (t, J 8.8 Hz, 1H), 7.34 (d, J 8.6 Hz, 1H). GCMS (Method S) [M]⁻ 187, RT 3.40 minutes (95.5%).

Intermediate 2

[2-(Difluoromethoxy)-6-fluorophenyl]methanamine

In a steel autoclave under an argon atmosphere, Raney nickel (~8 g, 50 wt % slurry in water) was added to a solution of Intermediate 1 (44.5 g, 214 mmol, 90% pure) in methanolic ammonia (7M, 400 mL). The reaction mixture was stirred vigorously under a 10 bar atmosphere of hydrogen until no further consumption of hydrogen was observed. The reaction mixture was filtered over a layer of kieselguhr, then the filtrate was partially concentrated (>225 mbar, 40° C.) to give the title compound (146.1 g) as a green liquid, which was used without further purification. GCMS (Method S) [M−H]⁺190, RT 3.35 minutes (87% purity).

Intermediate 3

5-Bromo-N-[2-(difluoromethoxy)-6-fluorobenzyl]-2-nitroaniline

Potassium carbonate (22.11 g, 160 mmol) was added to a solution of 4-bromo-2-fluoro-1-nitrobenzene (32 g, 145 mmol) and Intermediate 2 (30.6 g, 160 mmol) in 1-methyl-2-pyrrolidinone (320 mL). The resulting mixture was stirred at 80° C. for 5 h. After cooling to room temperature, the reaction mixture was diluted with ethyl acetate (~750 mL) and water (~750 mL). The layers were separated and the aqueous phase was extracted with ethyl acetate (500 mL). The combined organic layers were washed with water (7×200 mL) and brine (2×250 mL), then dried ($Na_2SO_4$), filtered, concentrated in vacuo and co-evaporated from diethyl ether, to give the title compound (68.6 g) as a dark yellow/orange solid, which was used without further purification. $\delta_H$(300 MHz, $CDCl_3$) 8.35 (br s, 1H), 8.02 (d, J 9.1 Hz, 1H), 7.44-7.23 (m, 2H), 7.02 (t, J 8.8 Hz, 2H), 6.78 (dd, J 9.1, 1.9 Hz, 1H), 6.63 (t, J72.8 Hz, 1H), 4.58 (d, J5.8 Hz, 2H). LCMS (SC_ACID) [M+H]⁺ 391/393 (Br pattern), RT 2.31 minutes (85% purity).

Intermediate 4

6-Bromo-1-[2-(difluoromethoxy)-6-fluorobenzyl]-2-methyl-1H-benzimidazole

Zinc powder (34.4 g, 527 mmol) was added to a solution of Intermediate 3 (68.68 g, 176 mmol) in acetic acid (350 mL). The resulting mixture was stirred at reflux for 1 h, after which time additional zinc (34.4 g, 527 mmol) was carefully added. The reaction mixture was heated at reflux for a further 18 h, then cooled to room temperature without stirring. The thick suspension was filtered over a glass filter and washed with ethyl acetate. The filtrate was concentrated in vacuo and the oily residue was stirred in ethanol (500 mL) for 2 h. The white solid which crystallised was collected by filtration and suspended in DCM (600 mL). The organic layers were washed with water (3×200 mL), dried ($Na_2SO_4$), filtered and concentrated in vacuo, to give the title compound (31.1 g, 45%) as a white solid. $\delta_H$(300 MHz, DMSO-d6) 7.57 (d, J1.8 Hz, 1H), 7.55-7.43 (m, 2H), 7.35 (t, J72.7 Hz, 1H), 7.25 (dd, J8.5, 1.8 Hz, 1H), 7.23-7.15 (m, 1H), 7.15-7.09 (m, 1H), 5.46 (s, 2H), 2.53 (s, 3H). LCMS (AN_ACID) [M+H]⁺ 385/387 (Br pattern), RT 1.79 minutes (98% purity).

Example 1

2-(5-{1-[2-(Difluoromethoxy)-6-fluorobenzyl]-2-methyl-1H-benzimidazol-6-yl}-pyrimidin-2-yl)propan-2-ol A solution of Intermediate 4 (12.88 g, 33.4 mmol), 2-[5-(4,4,5,5-tetramethyl-1,3,2-dioxaborolan-2-yl)pyrimidin-2-yl]propan-2-ol (9.72 g, 36.8 mmol) and sodium carbonate (10.63 g, 100 mmol) in a mixture of 1,4-dioxane (250 mL) and water (25 mL) was flushed with argon. [1,1'-Bis(diphenylphosphino)ferrocene]dichloropalladium(II) (0.819 g, 1.003 mmol) was added and the resulting mixture was stirred at reflux for 1 h. After cooling to room temperature, the reaction mixture was combined with the reaction mixture of a repeat of the same experiment, starting from Intermediate 4 (18.26 g, 47.4 mmol) and 2-[5-(4,4,5,5-tetramethyl-1,3,2-dioxaborolan-2-yl)pyrimidin-2-yl]propan-2-ol (13.77 g, 52.1 mmol), then stirred overnight. The solids (salts), including most of the water content, were removed by decantation and washed with diethyl ether. The combined organic layers were diluted with diethyl ether to a volume of ~1000 mL, then dried ($Na_2SO_4$), filtered and concentrated in vacuo. The residue was purified by filtration over a plug of silica (50-100% EtOAc in heptane) and the product-containing fractions were concentrated in vacuo to a volume of ~100-200 mL, whereupon the product started to crystallise. The solids were filtered off, washed with ethyl acetate and dried, to give the title compound (24.8 g, 69%) as a creamy white solid. The combined filtrates were concentrated in vacuo and triturated from diethyl ether overnight. The precipitate was filtered and dried, to give a second crop of the title compound (5.82 g, 16%) as a beige solid. $\delta_H$(300 MHz, DMSO-$d_6$) 9.03 (s, 2H), 7.78 (br s, 1H), 7.65 (d, J8.3 Hz, 1H), 7.56 (dd, J8.4, 1.7 Hz, 1H), 7.54-7.45 (m, 1H), 7.37 (t, J73.1 Hz, 1H), 7.24-7.11 (m, 2H), 5.55 (s, 2H), 5.11 (s, 1H), 2.58 (s, 3H), 1.55 (s, 6H). LCMS (AN_ACID) $[M+H]^+$ 443, RT 2.26 minutes (99% purity).

The invention claimed is:

1. 2-(5-{1-[2-(Difluoromethoxy)-6-fluorobenzyl]-2-methyl-1H-benzimidazol-6-yl}pyrimidin-2-yl)propan-2-ol, or a pharmaceutically acceptable salt thereof.

2. A pharmaceutical composition comprising 2-(5-{1-[2-(difluoromethoxy)-6-fluorobenzyl]-2-methyl-1H-benzimidazol-6-yl}pyrimidin-2-yl)propan-2-ol, or a pharmaceutically acceptable salt thereof, in association with a pharmaceutically acceptable carrier.

3. The pharmaceutical composition as claimed in claim 2 further comprising an additional pharmaceutically active ingredient.

4. A method for the treatment of disorders for which the administration of a modulator of TNFα function is indicated which comprises administering to a patient in need of such treatment an effective amount of 2-(5-{1-[2-(difluoromethoxy)-6-fluorobenzyl]-2-methyl-1H-benzimidazol-6-yl}pyrimidin-2-yl)-propan-2-ol, or a pharmaceutically acceptable salt thereof.

5. A method for the treatment of myocardial infarction, leukemia, melanoma, sarcoma, breast cancer, ovarian cancer, pancreatic cancer, renal cell carcinoma, prostate cancer, rheumatoid arthritis, Crohn's disease, multiple sclerosis and inflammatory bowel disease, which comprises administering to a patient in need of such treatment an effective amount of 2-(5-{1-[2-(difluoromethoxy)-6-fluorobenzyl]-2-methyl-1H-benzimidazol-6-yl}pyrimidin-2-yl)propan-2-ol, or a pharmaceutically acceptable salt thereof.

* * * * *